(12) United States Patent
Liang

(10) Patent No.: US 6,909,465 B2
(45) Date of Patent: Jun. 21, 2005

(54) SURGICAL LAMP HANDLE ASSEMBLY WITH BUILT-IN VIDEO CAMERA

(75) Inventor: Jyh-Wei Liang, Taipei (TW)

(73) Assignee: Mediline Enterprise Corporation, Tao Yuan Hsien (TW)

( * ) Notice: Subject to any disclaimer, the term of this patent is extended or adjusted under 35 U.S.C. 154(b) by 487 days.

(21) Appl. No.: 09/785,309

(22) Filed: Feb. 20, 2001

(65) Prior Publication Data

US 2002/0113890 A1 Aug. 22, 2002

(51) Int. Cl.$^7$ ............................................. H04N 5/225
(52) U.S. Cl. .................... 348/373; 348/143; 600/249
(58) Field of Search ................................ 348/143, 373; 600/247, 248, 249

(56) References Cited

U.S. PATENT DOCUMENTS

| | | | |
|---|---|---|---|
| 5,803,905 A | * | 9/1998 | Allred et al. ............... 600/249 |
| 6,290,645 B1 | * | 9/2001 | Goldfarb et al. ............ 600/249 |
| 6,402,351 B1 | * | 6/2002 | Borders et al. ............. 362/395 |
| 6,633,328 B1 | * | 10/2003 | Byrd et al. ................. 348/143 |
| 2002/0191389 A1 | * | 12/2002 | Hill ............................ 362/85 |

* cited by examiner

Primary Examiner—Wendy R. Garber
Assistant Examiner—Gary C. Vieaux
(74) Attorney, Agent, or Firm—Birch, Stewart, Kolasch & Birch, LLP

(57) ABSTRACT

A handle assembly with built-in video camera controlling a lamp lifting device for a surgical lamp by rotating some angles for adjusting the light's illumination zone, when focused on a planar surface. The handle assembly has a stationary disk which separates the video camera from a rotation device for the handle, so that the rotation of the handle for adjusting an illumination zone will not affect video camera picture shooting angle. The handle further has a gear set and belt located inside for transmitting the rotation of the handle to the lamp bracket lifting device for adjusting the light's illumination zone without moving the video camera shooting angle. In order to prevent the rotation of the handle from affecting the adjustment of the picture angle of the video camera, the stationary disk has a rotary inner ring for mounting the video camera and a stationary outer ring for engaging with the rotation device of the handle. It thus resolves the conventional problem of allowing both rotation of the video camera and adjustment of the light projection scope.

15 Claims, 3 Drawing Sheets

SURGICAL LAMP HANDLE ASSEMBLY WITH BUILT-IN VIDEO CAMERA

FIELD OF THE INVENTION

This invention relates to a surgical lamp handle assembly with a built-in camera, and especially to a surgical lamp handle that is capable of adjusting its illumination zone and built-in video camera's picture angle separately.

BACKGROUND OF THE INVENTION

Surgical lamp is an important facility used to illuminate surgery sites. A desirable surgical lamp should be at least having a proper light color, illumination intensity and adjustable light field or illumination zone. In a surgery, the operation incision may be very small and needs only the light focusing on a small scope. However, the injured area could be relative large in case it is a treatment for a burned or scalded body surface, the illumination zone should be enlarged to cover a relatively bigger area. Thus, to adjust and change the illumination zone is an indispensable function for a surgical lamp assembly.

With reference to FIG. 1, a conventional surgical lamp which generally comprising a housing P20, a reflector P21 is arranged concentrically inside the housing P20, and a transparent shield P22. Between the reflector and transparent shield, there is a mechanism for reciprocally moving the position of the lamp bracket P23 up or down, whereby to change light reflection angle through the reflector P21 to a illumination plane. The mechanism comprising a trapezoidal rod P24 engaged with a pin and connected to an outer sleeve. As illustrated in FIG. 1, the trapezoidal rod P24 connected with one end of the handle P10 in a same axis. Hence when the trapezoidal rod P24 is turned by handle P10, the pin will lift or lower the sleeve and consequently move the lamp bracket P23 upward or downward.

In other words, turning the handle P10 may change the reflection angle of the lamp, and change the size of the lamp's illumination zone. Furthermore, it is essential to use a sterilized handle P11 to cover the light handle P10 in a surgery, and the handle P11 should be sterilized after every operation. To this end, a connect means P12 is provided for connecting or releasing the sterilized handle P11 and enables the sterilized handle P11 could be removed for sterilization treatment after each surgery is completed.

In addition to the surgical lamp, a surgical video camera is another important facility in the surgery site. It is used for capturing the surgical area and surgery steps took by the surgeon. Said surgical video camera is generally being positioned above the surgeon's head at the same height of the surgical lamp. Therefore, to combine the surgical lamp and surgical video camera together shall gain a great advantages of making the facility multifunctional and saves a lot of space in the surgery site.

There is a surgical lamp with a built-in video camera inside being introduced to the market place. The built-in video camera can be manually or electrically turned to change the lens angle as desired by the operators, but said surgical lamp cannot be adjusted to change the scope of its illumination. Hence although said product has multiple function and makes better utilization of space, it sacrifices the basic requirements of adjusting illumination zone in the surgical sites. This leaves rooms for improvement.

SUMMARY OF THE INVENTION

In view of aforesaid disadvantages, it is therefore an object of this invention to provide a structure that enables controlling of the video camera rotation and handle movement totally independent with each other whereby to resolve the problem set forth above.

In one aspect, the handle according to this invention includes a stationary disk which has a rotary inner ring and a stationary outer ring. The rotary inner ring has a video camera mounted thereon, and the stationary outer ring engages with a lifting means of a lamp bracket. Turning the handle will drive a transmission means to move the lifting means. As the inner and outer ring are separated without engaging with each other, when the lamp bracket is moving, the video camera will keep stationary. On the other hand, when the inner ring is turning and rotating the video camera, the handle and lifting means will remain stationary. Hence the conventional problem of able to turn the video camera shooting angle but cannot adjust the lamp's illumination zone will be resolved.

BRIEF DESCRIPTION OF THE DRAWINGS

The invention may take form in various components and arrangements of components, and in various steps and arrangements of steps. The drawing is only for purposes of illustrating a preferred embodiment and is not to be construed as limiting the invention.

DESCRIPTION OF THE PREFERRED EMBODIMENT

Figure 2:
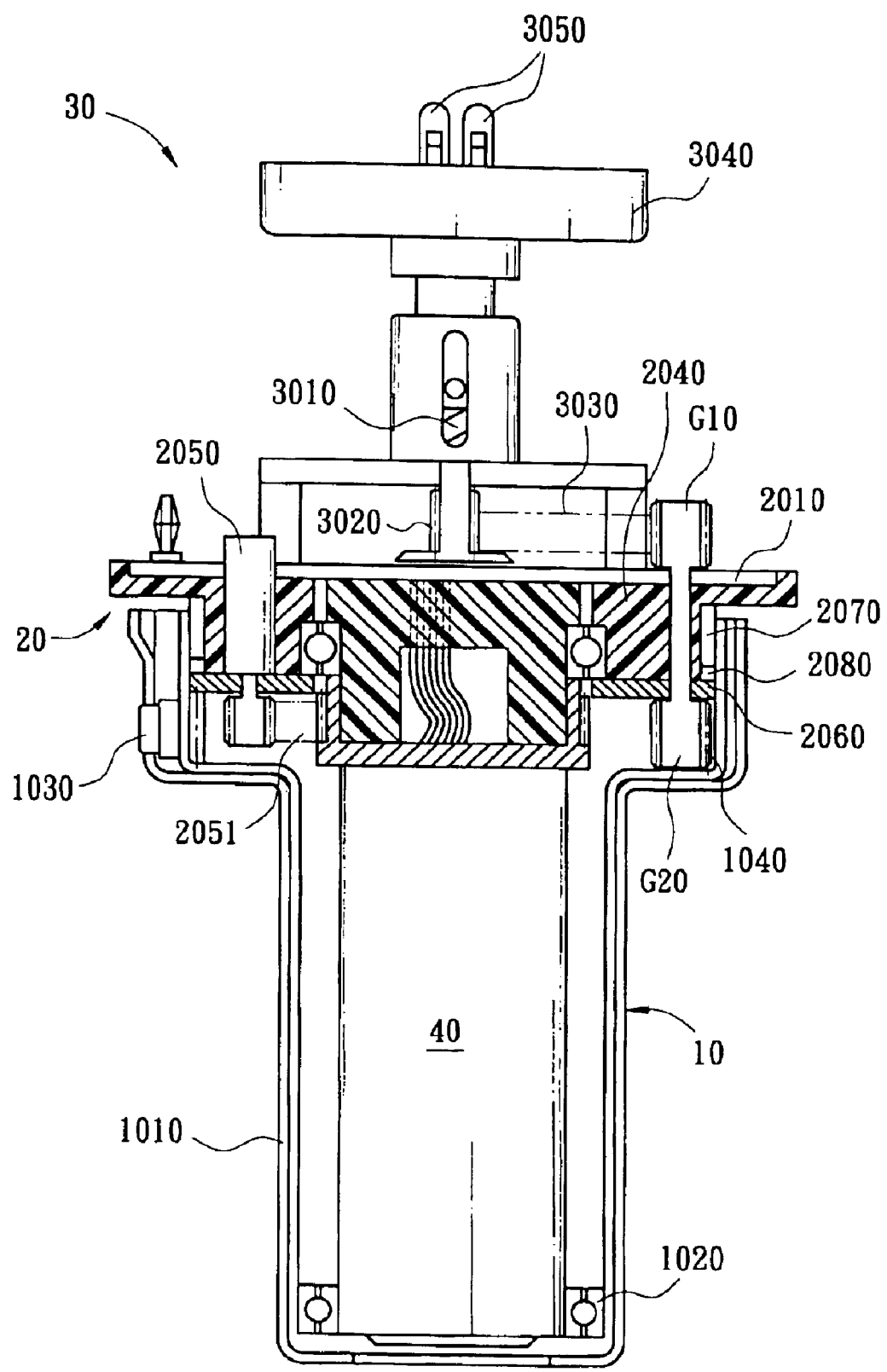
FIG. 2 is a fragmentary side sectional view of this invention.

Referring to FIG. 2, the surgical lamp having built-in video camera according to this invention includes at least a handle 10, a stationary disk 20 and a lifting means 30. The handle 10 is substantially a barrel casing having a sterilization handle 1010 at the outer side which may be engaged or removed by means of a snap button 1030. At one end of the handle 10, there is an inner gear 1040 engageable with a first gear G20 of a transmission means. The top end of the handle 10 engages with a metal ring 2070 which surrounds an outer ring 2040 of the stationary disk 20. There is a TEFLON washer 2080 located under the metal ring 2070 for reducing rotation friction. A press board 2060 is provided to engage with the outer ring 2040. Hence the handle 10 may rotate relatively against the stationary disk 20 without breaking away. For disassembling the stationary disk 20 and handle 10, the metal ring 2070 should be removed first from the handle 10.

Figure 1:
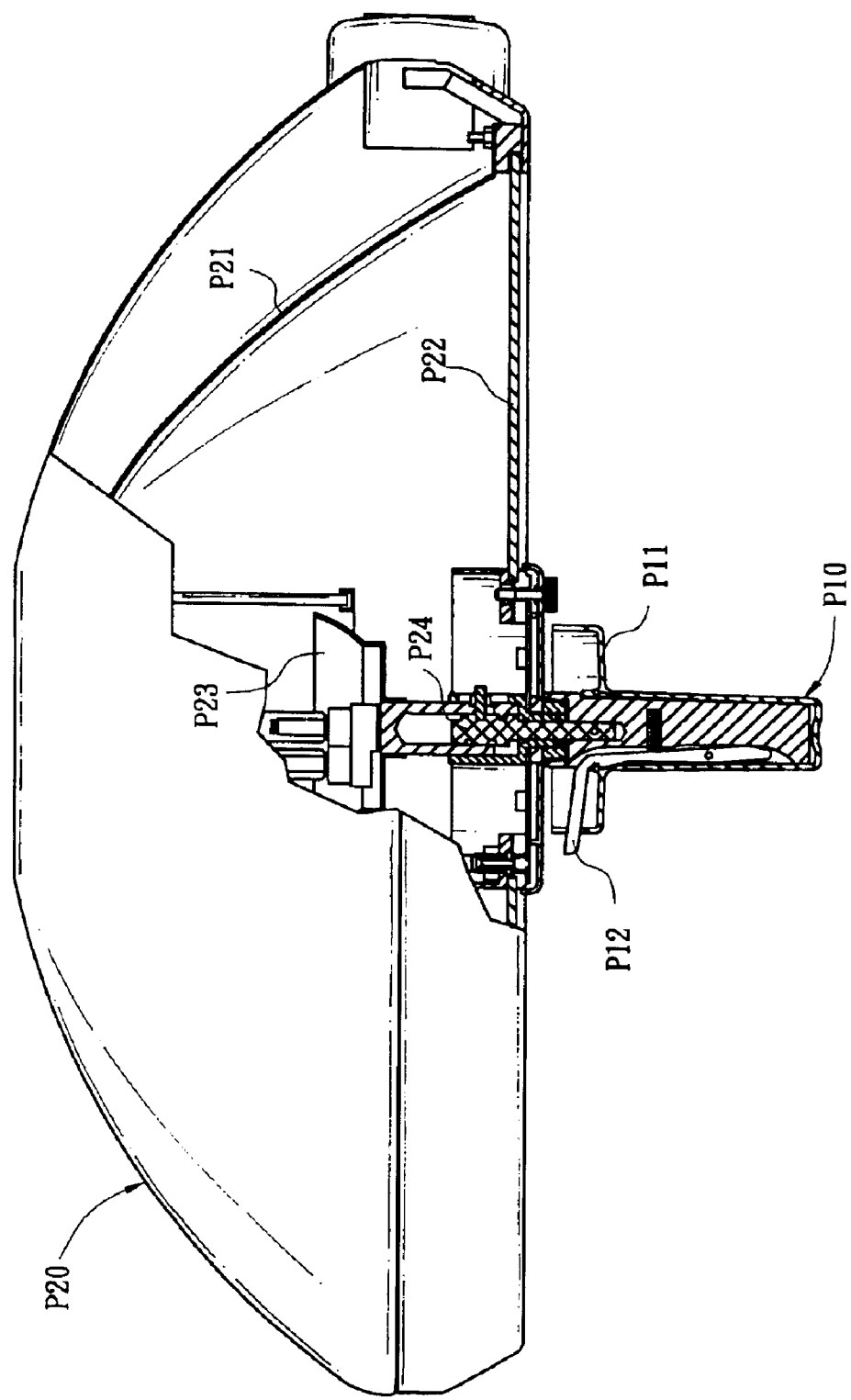
FIG. 1 is a schematic side sectional view of a conventional surgical lamp.
Figure 3:
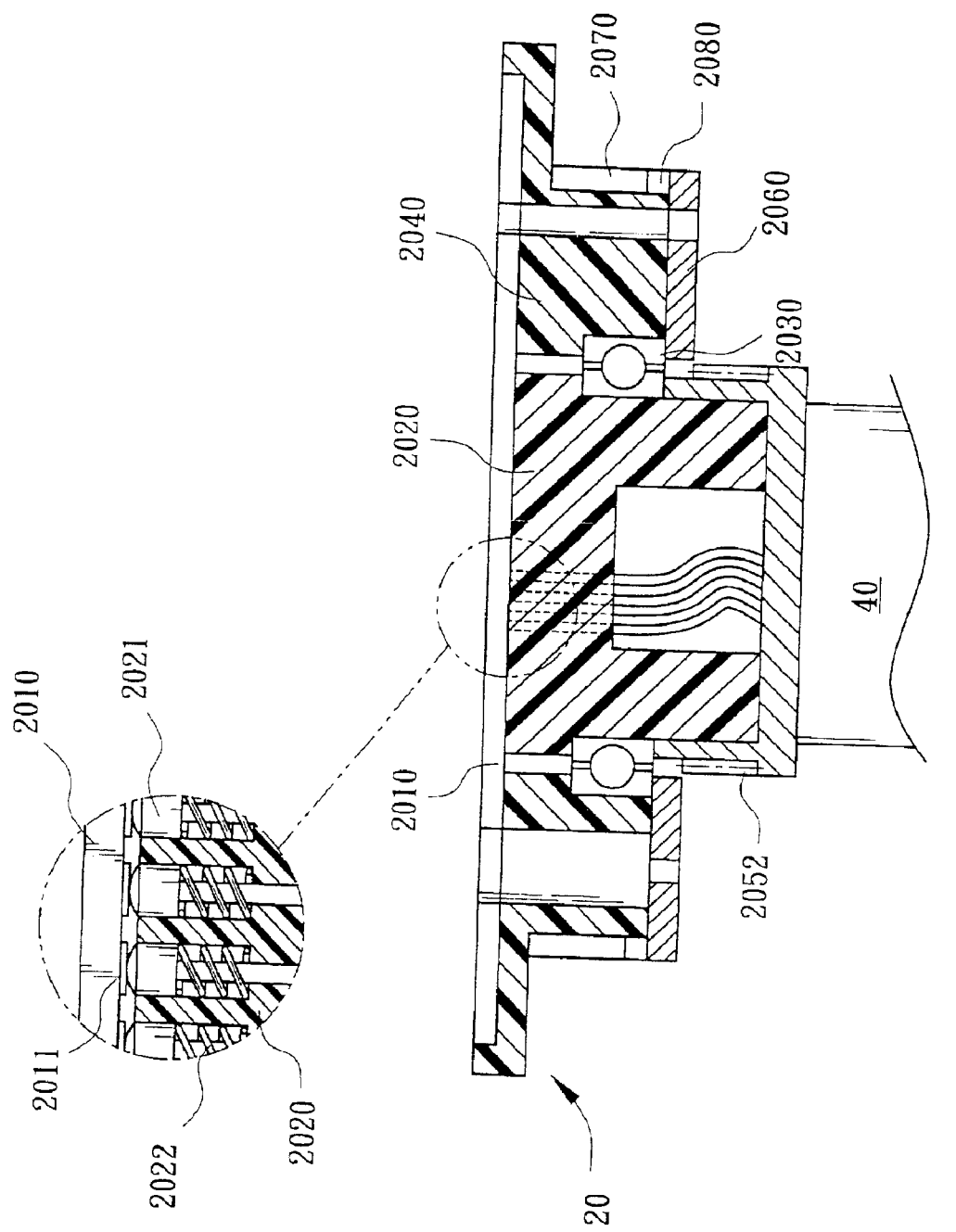
FIG. 3 is a fragmentary side sectional view of this invention, showing the stationary disk structure.

Referring to FIG. 3, the stationary disk 20 is housed in the handle 10 and includes the stationary outer ring 2040 and a turnable inner ring (unmarked) with a first ball bearing 2030 interposed therebetween as a rotational interface. There is a circuit board 2010 mounted on the outer ring 2040 for receiving, transmitting or controlling power supply and video and audio signals. Above the circuit board 2010, a lifting means 30 is provided which has a trapezoidal rod 3010 and a sleeve like the one shown in FIG. 1 for lifting or lowering the lamp bracket 3040 located thereabove for changing the relative position between the light bulb 3050 and the reflector (not shown in the figure). The motion of the trapezoidal rod 3010 and handle 10 are linked by means of the transmission means which includes a second gear 3020 engaged with the trapezoidal rod 3010, a first transmission belt 3030, and first gears G10 and G20. The first gears G10 and G20 engage with a common shaft which runs through the circuit board 2010, stationary disk 20, outer ring 2040 and press board 2060. The first gear G20 engages with the inner gear 1040 of the handle 10. Hence when the handle 10 turns, the rotation of the handle will be transmitted through the first gear G10, first belt 3030, second gear 3020 and trapezoidal rod 3010 whereby to drive the lifting means 30 upward or downward to change light projection scope.

Referring to FIG. 2, the video camera 40 is housed in the handle 10 and attached to the inner ring of the stationary disk 20. The first ball bearing 2030 is located between the inner ring and outer ring 2040 to serve as a rotation interface. The handle 10 and lifting means 30 are mounted on the outer ring 2040. Hence the rotation of the handle 10 for driving the lifting means 30 does not affect the video camera 40 mounted on the inner ring of the stationary disk 20. Referring to FIGS. 2 and 3, the inner ring has a third gear 2052. At the outer ring 2040 or press board 2060, there is a motor 2050 mounted thereon which engages with a fourth gear (unmarked) and a second transmission belt 2051 which in turn engages with the third gear 2052. Hence by controlling the motor 2050 to rotate clockwise or counterclockwise, the video camera 40 may be turned to an angle desired for adjusting picture shooting angle.

In the handle 10, a second ball bearing 1020 may be provided between the video camera 40 and handle 10 at another end thereof to enable the video camera 40 be held in the handle 10 securely and rotating smoothly at the same axis of the handle 10.

Referring to FIG. 3, in order to enable the video camera 40 to transmit power supply and video and audio signals effectively, the inner ring may be changed to a terminal board 2020 made from an insulation material. And springs 2022 are provided to make the terminal contacts 2021 of power supply and video and audio signal cable pressing against an annular conductive ring 2011 located on the circuit board 2010. When the circuit board 2010 turns relatively against the terminal board 2020, electrical passage between the circuit board 2010 and terminal contacts 2021 will be maintained constantly. Hence the video camera 40 may be turned clockwise or counterclockwise continuously over 360 degree without power supply and signal interruption.

In summary, this invention employs the inner and outer ring of the stationary disk to make the rotation means of the video camera and rotation means of the handle independent from each other. It thus resolves the conventional problem of capable to rotate the video camera but cannot adjust the light projection scope.

It is to be noted that transmission means for transmitting rotation of the handle to the lifting means of the lamp bracket has many other alternatives besides the belt and gears construction set forth above.

It may thus be seen that the objects of the present invention set forth herein, as well as those made apparent from the foregoing description, are efficiently attained. While the preferred embodiment of the invention has been set forth for purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A surgical lamp handle assembly with a built-in video camera, comprising at least:
   a handle having a barrel casing and an inner gear located at one end thereof;
   a stationary disk located in the handle having a rotary inner ring and a stationary outer ring, the outer ring having a circuit board and a lamp bracket lifting means mounted thereon;
   a video camera located in the handle and attached to the rotary inner ring; and
   a transmission means for transmitting the rotation of the handle to control the lamp bracket lifting means moving upwardly or downwardly.

2. The surgical lamp handle assembly as claimed in claim 1, wherein said transmission means further includes:
   a second gear engaged with the lamp bracket lifting means at a lower section thereof;
   a first transmission belt engaged with the second gear; and
   a gearing means which includes a pair of first gears and a shaft, said first gears being mounted at two ends of the shaft, and the shaft being running through the outer ring, one of the first gear being engaged with the inner gear and another one of the first gear being engaged with the first transmission belt for driving the second gear to control the lamp bracket lifting means moving upwardly or downwardly.

3. The surgical lamp handle assembly as claimed in claim 1 further comprising a first ball bearing located between the inner and outer ring for reducing friction incurred by rotation of the inner ring.

4. The surgical lamp handle assembly as claimed in claim 1 further having a second ball bearing located between one end of the video camera and the handle for reducing friction between the video camera and inner surface of the handle incurred by rotation of the video camera.

5. The surgical lamp handle assembly as claimed in claim 1, wherein the handle further has a sterilization handle located outside thereof engaged with the handle through a snap button.

6. The surgical lamp handle assembly as claimed in claim 1, wherein the outer ring of the stationary disk is surrounded by a rotary metal ring, the metal ring being engaged with the handle for the handle to rotate relatively against the stationary disk.

7. The surgical lamp handle assembly as claimed in claim 6, wherein the outer ring has a TEFLON washer located at the circumference thereof for reducing friction between the stationary disk and handle.

8. The surgical lamp handle assembly as claimed in claim 1, wherein the inner ring has a terminal board which has a plurality of terminal contacts to make electrical contact with the circuit board for transmitting electric power, control signals or video audio signals.

9. The surgical lamp handle assembly as claimed in claim 8, wherein the terminal board is made of insulation material.

10. The surgical lamp handle assembly as claimed in claim 9, wherein the insulation material is bakelite.

11. The surgical lamp handle assembly as claimed in claim 9, wherein the insulation material is engineering plastics.

12. The surgical lamp handle assembly as claimed in claim 8, wherein the terminal board has springs for the terminal contacts to make desired contact with the circuit board.

13. The surgical lamp handle assembly as claimed in claim 8, wherein the terminal board has a plurality of conductive rings each maintaining contact with one terminal contact when the terminal board is turning.

14. The surgical lamp handle assembly as claimed in claim 1, wherein the video camera and inner ring are driven to rotate by a motor mounted on the outer ring located on the stationary disk.

15. The surgical lamp handle assembly as claimed in claim 14, wherein the inner ring has a third gear engaged with a second transmission belt driven by the motor.

* * * * *